United States Patent [19]

Iijima et al.

[11] Patent Number: 4,882,340
[45] Date of Patent: Nov. 21, 1989

[54] BENZOFURAN DERIVATIVE AND PROCESSES FOR PREPARING THE SAME

[75] Inventors: Ikuo Iijima, Urawa; Masakatsu Ozeki, Wako; Yutaka Saiga, Ageo; Tohru Ishizuka, Kitamoto; Kunio Nosaka, Kasukabe, all of Japan

[73] Assignee: Tanabe Seiyaku Co., Ltd., Osaka, Japan

[21] Appl. No.: 239,754

[22] Filed: Sep. 2, 1988

[30] Foreign Application Priority Data

Sep. 4, 1987 [JP] Japan .................. 62-222754

[51] Int. Cl.$^4$ .................. C07D 307/78; C07D 405/2; A61K 31/34; A61K 31/445
[52] U.S. Cl. .................. 514/320; 514/469; 514/233.5; 514/422; 546/196; 544/153; 548/525; 549/467
[58] Field of Search .................. 549/467; 544/153; 546/196; 548/525; 514/422, 469, 470, 233.5, 320

[56] References Cited

U.S. PATENT DOCUMENTS

| | | | |
|---|---|---|---|
| 3,627,763 | 12/1971 | Jaeggi et al. | 549/467 |
| 3,689,507 | 9/1972 | Gates et al. | 549/467 |
| 4,107,437 | 8/1978 | Maffrand et al. | 549/467 |
| 4,153,716 | 5/1979 | Scherrer et al. | 549/467 |
| 4,751,230 | 6/1988 | Lavielle et al. | 544/153 |

OTHER PUBLICATIONS

Bradley et al., J. Clin. Pharm., 10:65–68, (1970).

Primary Examiner—Mary C. Lee
Assistant Examiner—F. Brendan Magrab
Attorney, Agent, or Firm—Birch, Stewart, Kolasch & Birch

[57] ABSTRACT

A novel benzofuran derivative of the formula:

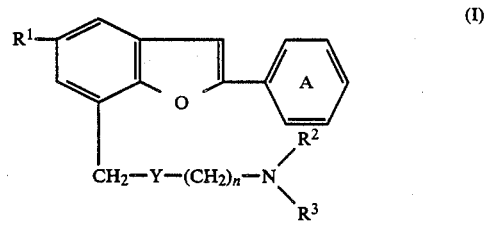

wherein $R^1$ is hydrogen atom, a lower alkoxy group or a halogen atom, one of $R^2$ and $R^3$ is a lower alkyl group and the other is a lower alkyl group or a phenyl-lower alkyl group, or $R^2$ and $R^3$ combine together with adjacent nitrogen atom to form a heteromonocyclic group, Ring A is a substituted or unsubstituted phenyl group, Y is oxygen atom or sulfur atom and n is an integer of 2 or 3, or a pharmaceutically acceptable salt thereof is disclosed.

The compound (I) or a pharmaceutically acceptable salt thereof has a potent inhibitory activity against reflective contractions of urinary bladder.

8 Claims, No Drawings

BENZOFURAN DERIVATIVE AND PROCESSES FOR PREPARING THE SAME

This invention relates to a novel benzofuran derivative and processes for preparing the same. More particularly, it relates to a benzofuran derivative of the formula:

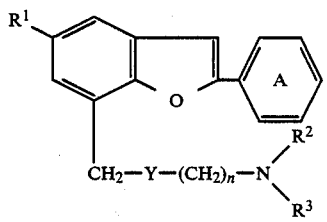
(I)

wherein $R^1$ is hydrogen atom, a lower alkoxy group or a halogen atom, one of $R^2$ and $R^3$ is a lower alkyl group and the other is a lower alkyl group or a phenyl-lower alkyl group, or $R^2$ and $R^3$ combine together with adjacent nitrogen atom to form a heteromonocyclic group, Ring A is a substituted or unsubstituted phenyl group, Y is oxygen atom or sulfur atom and n is an integer of 2 or 3, or a pharmaceutically acceptable salt thereof.

Pollakiuria (i.e., frequent micturition) is a symptom of diminution in effective bladder capacity and causes a person much trouble in his daily life. Since micturition is caused by reflective contraction of urinary bladder, a drug which inhibits the reflective contraction is useful for treatment of pollakiuria. A typical example of such drug is flavoxate (chemical name: 2-piperidinoethyl 3-methyl-4-oxo-2-phenyl-4H-1-benzopyran-8-carboxylate) [The Journal of Clinical pharmacology, Vol. 10, 65–68 (1970)[.

As a result of various investigations, we have now found that the compound (I) of the present invention or a salt thereof has potent inhibitory activity against the reflective contraction of the urinary bladder. For example, when the inhibitory activity against the reflective contraction of the urinary bladder was examined by administering a test compound into the duodenum of female rats, the inhibitory activity of 2-phenyl-5-methoxy-7-(2-piperidionoethylthiomethyl)-benzofuran of the present invention was more than 10 times as strong as that of flavoxate.

Representative examples of the compound of the present invention include those of the formula (I) in which $R^1$ is hydrogen atom, a lower alkoxy group (e.g., methoxy, ethoxy, propoxy or butoxy) or a halogen atom (e.g., fluorine, chlorine or bromine); one of $R^2$ and $R^3$ is a lower alkyl group (e.g., methyl, ethyl, propyl or butyl) and the other is a lower alkyl group (e.g., methyl, ethyl, propyl or butyl) or a phenyl-lower alkyl group (e.g., benzyl), or $R^2$ and $R^3$ combine together with adjacent nitrogen atom to form a heteromonocyclic group (e.g., pyrrolidino, piperidino or morpholino group); Ring A is phenyl group or a phenyl group substituted with a lower alkyl group (e.g., methyl, ethyl, propyl or butyl), a lower alkoxy group (e.g., methoxy, ethoxy, propoxy or butoxy) or a halogen atom (e.g., fluorine, chlorine or bromine); Y is oxygen atom or sulfur atom; and n is an integer of 2 or 3.

Among them, a prefered subgenus includes those of the formula (I) in which $R^1$ is hydrogen atom, methoxy or chlorine, $R^2$ is methyl or ethyl, $R^3$ is methyl, ethyl or benzyl, or $R^2$ and $R^3$ combine together with adjacent nitrogen atom to form pyrrolidino, piperidino or morpholino group, Ring A is phenyl, methylphenyl, methoxyphenyl or chlorophenyl, Y is oxygen atom or sulfur atom and n is 2 or 3.

Another preferred subgenus is those of the formula (I) in which $R^1$ is hydrogen atom, methoxy or chlorine, $R^2$ is methyl or ethyl, $R^3$ is methyl, ethyl or benzyl, or $R^2$ and $R^3$ combine together with adjacent nitrogen atom to form pyrrolidino, piperidino or morpholino group, Ring A is phenyl, 4-methylphenyl, 4-methoxyphenyl or 4-chlorophenyl, Y is oxygen atom or sulfur atom and n is 2 or 3.

Further preferred subgenus is those of the formula (I) in which $R^1$ is hydrogen or methoxy, $R^2$ and $R^3$ combine together with adjacent nitrogen atom to form piperidino group, Ring A is phenyl, Y is sulfur atom and n is 2.

According to the present invention, the compound (I) can be prepared, for example, by reacting a benzofuran compound of the formula:

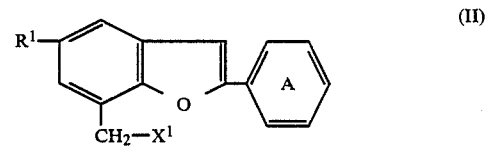
(II)

wherein $X^1$ is a reactive residue and $R^1$ and Ring A are the same as defined above, with an amine compound of the formula:

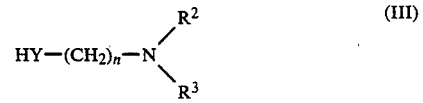
(III)

wherein $R^2$, $R^3$, Y and n are the same as defined above, or a salt thereof, or by reacting a benzofuran compound of the formula:

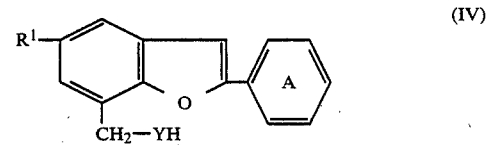
(IV)

wherein $R^1$, Ring A and Y are the same as defined above, with an amine compound of the formula:

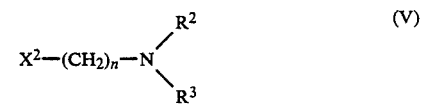
(V)

wherein $X^2$ is a reactive residue and $R^2$, $R^3$ and n are the same as defined above, or a salt thereof.

Examples of the reactive residue ($X^1$ or $X^2$) in the starting compound (II) or (V) include, for example, a halogen atom such as fluorine, chlorine or bromine, a lower alkylsulfonyloxy group such as methanesulfonyloxy group, or a substituted or unsubstituted arylsulfonyloxy group such as toluenesulfonyloxy group. Examples of the salt of the starting compound (III) or (V) include, for example, hydrochloride, hydrobromide, sulfate, and the like.

The reaction of the compound (II) with the compound (III) or its salt and the reaction of the compound (IV) with the compound (V) or its salt can be conducted in the presence or absence of an acid acceptor. Examples of the acid acceptor include, for example, an alkali metal hydroxide (e.g., sodium hydroxide or potassium hydroxide), an alkali metal carbonate (e.g., sodium carbonate or potassium carbonate), an alkali metal bicarbonate (e.g., sodium bicarbonate or potassium bicarbonate), an alkali metal hydride (e.g., sodium hydride), an alkali metal alkoxide (e.g., sodium methoxide or sodium ethoxide) trialkylamine (e.g., trimethylamine or triethylamine) or pyridine. Lower alkanol, tetrahydrofuran, dioxane, dimethylformamide and dimethylsulfoxide are suitable as the solvent. It is preferred to carry out these reactions at a temperature of 0° to 100° C.

The compound (I) thus obtained can easily be converted to a salt thereof by a conventional method (e.g., acid treatment).

As mentioned hereinbefore, the compound (I) and a salt thereof have a potent inhibitory activity against the reflective contraction of urinary bladder. Therefore, the compound (I) and a salt thereof are useful for treatment and/or prophylaxis of urinary system diseases associated with contracting function disorder of urinary bladder or ureter, for example, pollakiuria (frequent micturition), dyuria (painful urination), nocturia (voiding during the night, enuresis (bed-wetting at night), irritable bladder, and the like.

The compound (I) of the present invention can be used for pharmaceutical use either in the free form or in the form of a pharmaceutically acceptable salt thereof. Examples of the salt of the compound (I) include inorganic acid addition salts such as hydrochloride, hydrobromide or sulfate, and organic acid addition salts such as oxalate, sulfamate, acetate, fumarate, maleate, citrate or methanesulfonate.

The compound (I) or a salt thereof can be administered either orally or parenterally. For oral administration, the compound (I) or a salt thereof may be used in the solid form such as tablets, powders, capsules or granules, which may contain conventional carriers binders, diluents, disintegrators, wetting agents and the like. They may also be used in liquid form such as aqueous or oily suspensions, solutions, syrups or elixirs. On the other hand, for parenteral administration, the compound (I) or a salt thereof may be used, for example, in the form of injections.

The dose of the compound (I) or a salt thereof may vary over a wide range depending on the administration route, the age, body weight or conditions of patients and the kind and severity of diseases to be treated. In general, however, preferred daily dose of the compound (I) or a salt thereof is in the range of 0.01 to 100 mg/kg/day; especially 0.1 to 30 mg/kg/day in case of oral administration, or 0.05 to 10 mg/kg/day in case of parenteral administration.

The starting compound (II) or (IV) can be prepared by the method mentioned below. Namely, a benzofuran-7-carboxylic acid compound of the formula:

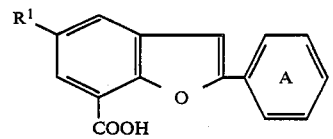

wherein $R^1$ and Ring A are the same as defined above, or a lower alkyl ester thereof is reduced with a reducing agent (e.g., lithium aluminum hydride) to give the compound (IV) (Y=oxygen atom), and the hydroxy group of the product is converted to the reactive residue to give the starting compound (II). Moreover, the compound (II) is treated with thiourea to give the compound (IV) (Y=sulfur atom).

Throughout the specification and claims, the terms "lower alkyl" and "lower alkoxy" should be interpreted as referring to straight or branched alkyl of one to 4 carbon atoms and straight or branched alkoxy of one to 4 carbon atoms, respectively.

EXPERIMENT 1

(Intravenous administration)

Sprague-Dawley female rats (body weight: 200–300 g) were anesthetized with urethane (1.1 g/kg, S.C.). After the abdomen was incised, a catheter was inserted into the tip of the urinary bladder and one end of the catheter was connected to a syringe. A physiological saline solution was continuously injected into the urinary bladder via the syringe at constant speed, and the micturition intervals were examined continuously. A test compound (dose: 2 mg/kg) dissolved in a physiological saline solution was administered into the femoral vein. The micturition interval obtained after administration of the test compound was compared with those obtained before administration, and the inhibitory activity of the test compound against contractions of urinary bladder was estimated in terms of "micturition interval ratio" which is calculated by the following formula:

$$\text{Micturition interval ratio} = \frac{\text{Maximum micturition interval (minutes) obtained for 30 minutes after administration of the test compound}}{\text{Average of 3 micturition intervals (minutes) obtained before administration of the test compound}}$$

(Results)

The micturition interval ratio of all of compounds shown in Table 1 were more than 1.4.

TABLE 1

Structure:
R¹-substituted benzofuran with 2-phenyl group and CH₂—Y—(CH₂)ₙ—NR²R³ substituent

| R¹ | -NR²R³ | Y | n | Salts |
|---|---|---|---|---|
| H | -N(piperidino) | S | 2 | Oxalate |
| CH₃O | -N(piperidino) | S | 2 | Oxalate |
| H | -N(piperidino) | S | 3 | Oxalate |
| H | -N(CH₃)₂ | S | 2 | Hydrochloride |
| H | -N(C₂H₅)₂ | S | 2 | Oxalate |
| H | -N(morpholino) | S | 2 | Hydrochloride |
| H | -N(CH₃)(CH₂Ph) | S | 2 | Hydrochloride |
| H | -N(piperidino) | O | 2 | Hydrochloride |
| H | -N(piperidino) | O | 3 | Oxalate |

EXPERIMENT 2

(Duodenal administration)

Sprague-Dawley female rats (body weight: 200–300 g) were anesthetized with urethane (1.1 g/kg, s.c.). An aqueous 5% mannitol solution was continuously injected into femoral vein at a speed of 0.06 ml/minute, and micturition intervals (minutes) were examined. A test compound dissolved in water was administered into duodenum. The micturition interval obtained after administration of the test compound was compared with that obtained before administration, and the inhibitory activity of the test compound against contractions of urinary bladder was estimated in terms of "micturition interval ratio" which is calculated by the following formula:

$$\text{Micturition interval ratio} = \frac{\text{Maximum micturition interval (minutes) obtained for 2 hours after administration of the test compound}}{\text{Maximum micturition interval (minutes) obtained for 2 hours before administration of the test compound}}$$

(Results)

The micturition interval ratio of 2-phenyl-7-(2-piperidinoethylthiomethyl)benzofuran oxalate of the present invention at a dose of 30 mg/kg was 2.7. On the other hand, the micturition interval ratio of flavoxate hydrochloride at a dose of 100 mg/kg was 1.3.

EXPERIMENT 3

(Duodenal administration)

Sprague-Dawley female rats (body weight: 200–300 g) were anesthetized with urethane (1.1 g/kg, s.c.). The urine produced in kidney during the experiment was discharged outside of the body via a polyethylene tube inserted into both ureters. Further, a polyethylene tube was inserted into urinary bladder via urethra meatus and one end of the polyethylene tube was connected with a transducer by which the change in intravesical pressure was measured. The urinary bladder was loaded with a physiological saline solution (0.5 ml) and bethanechol chloride dissolved in a physiological saline solution was continuously injected into vein at a speed of 53 µg/kg/minute. After it was confirmed that rhythmical contractions continued for at least 30 minutes, a test compound dissolved in distilled water was administered into duodenum at a volume of 0.1 ml/100 g. The number of contractions obtained after administration of the test compound was compared with that of contractions obtained before administration, and the inhibitory activity of the test compound against contractions of urinary bladder was estimated in terms of "inhibition ratio (%)" which is calculated by the following formula:

$$\text{Inhibition ratio (\%)} = \left(1 - \frac{\text{The minimum number of contractions obtained for each 15 minutes until 2 hours after administration of the test compound}}{\text{The number of contractions obtained for 15 minutes before administration of the test compound}}\right) \times 100$$

(Results)

The inhibition ratio of 2-phenyl-5-methoxy-7-(2-piperidinoethylthiomethyl)benzofuran oxalate of the present invention at a dose of 30 mg/kg was 67%. On the other hand, the inhibition ratio of flavoxate hydrochloride at a dose of 300 mg/kg was 28%.

EXAMPLE 1

(1) 2-Phenylbenzofuran-7-carboxylic acid (40 g) is dissolved in tetrahydrofuran (300 ml) and the solution is added dropwise to a suspension of lithium aluminum hydride (19.12 g) in tetrahydrofuran (130 ml) under ice-cooling. After the mixture is stirred at 70° C. for 2 hours, water is added to the mixture to decompose excess lithium aluminum hydride and its complex. Insoluble materials are filtered off, and the filtrate is concentrated under reduced pressure to remove solvent. The residue is dissolved in ethyl acetate, and the solution is washed with water, dried and concentrated under reduced pressure to remove solvent. The residue is recrystallized from a mixture of ethyl acetate and n-hexane, whereby 7-hydroxymethyl-2-phenylbenzofuran (34.4 g) is obtained. Yield: 91%.

m.p. 117.5°–118.5° C.

(2) Thionyl chloride (0.65 ml) is added to a mixture of 7-hydroxymethyl-2-phenylbenzofuran (1.0 g), pyridine (0.38 ml) and methylene chloride (8 ml) under ice-cooling, and the mixture is stirred at room temperature for 30 minutes. The mixture is concentrated under reduced pressure to remove solvent, and the residue is dissolved in ethyl acetate. The solution is washed with water, dried and concentrated under reduced pressure to remove solvent. The residue is recrystallized from n-hexane, whereby 7-chloromethyl-2-phenylbenzofuran (0.9 g) is obtained. Yield: 83%.

m.p. 72°–73° C.

(3) N-(2-Mercaptoethyl)piperidine (0.73 g) is added to a suspension of sodium hydride (60% oil dispersion) (0.2 g) in tetrahydrofuran (3 ml), and a solution of 7-chloromethyl-2-phenylbenzofuran (1.21 g) in tetrahydrofuran (3 ml) is added thereto. The mixture is stirred at room temperature for 2 hours and further refluxed for one hour. After cooling, the mixture is diluted with water and extracted with ethyl acetate. The extract is washed with water, dried and concentrated under reduced pressure to remove solvent. The residue is converted to its oxalate and recrystallized from ethanol, whereby 2-phenyl-7-(2-piperidinoethylthiomethyl)benzofuran oxalate (1.8 g) is obtained. Yield: 82%.

m.p. 187°–188° C.

EXAMPLE 2

A mixture of 7-chloromethyl-2-phenylbenzofuran (7.0 g), thiourea (2.5 g), water (2 ml) and ethanol (38 ml) is refluxed for 1.5 hours. A solution of sodium hydroxide (1.73 g) in water (18 ml) is added to the mixture, and the mixture is further refluxed for 1.5 hours. After cooling, the mixture is adjusted to pH 3 with 10% sulfuric acid and extracted with ethyl acetate. The extract is washed with water, dried and concentrated under reduced pressure to remove solvent. The residue (7-mercaptomethyl-2-phenylbenzofuran) is dissolved in ethanol (15 ml), and 4.7% potassium hydroxide-ethanol (100 ml) and N-(2-chloroethyl)piperidine hydrochloride (5.5 g) are added thereto. The mixture is stirred at 60° C. for one hour and concentrated under reduced pressure. The concentrate is diluted with water and extracted with ethyl acetate. The extract is washed with water, dried and concentrated under reduced pressure to remove solvent. The residue is recrystallized from isopropanol, whereby 2-phenyl-7-(2-piperidinoethylthiomethyl)benzofuran (8.43 g) is obtained. Yield: 83%.

m.p. 64.5°–65.5° C.

Hydrochloride of the product:

m.p. 196°–197° C. (recrystallized from ethanol).

EXAMPLES 3 TO 9

The corresponding starting compounds are treated in the same manner as described in Example 2, whereby the compounds shown in Table 2 are obtained.

TABLE 2

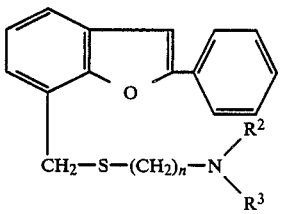

| Example Nos. | −N(R²)(R³) 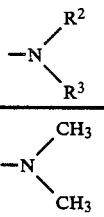 | n | Salts | m.p. (°C.) | Yield (%) |
|---|---|---|---|---|---|
| 3 | −N(CH₃)(CH₃) | 2 | HCl | 189.0–190.5 (isopropanol) | 80.2 |
| 4 | −N(C₂H₅)(C₂H₅) | 2 | Fumarate | 100–101.5 (isopropanol) | 78.2 |
| 5 | −N morpholino 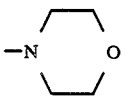 | 2 | HCl | 192.5–194.5 (isopropanol) | 73.1 |

TABLE 2-continued

Structure:
7-position: CH₂—S—(CH₂)ₙ—NR²R³ on benzofuran with 2-phenyl substituent

| Example Nos. | —N(R²)(R³) | n | Salts | m.p. (°C.) | Yield (%) |
|---|---|---|---|---|---|
| 6 | —N(pyrrolidinyl) | 2 | HCl | 201–202 (isopropanol) | 67.8 |
| 7 | —N(CH₃)(CH₂-phenyl) | 2 | HCl | 156–157 (isopropanol) | 77.4 |
| 8 | —N(CH₃)₂ | 3 | HCl | 153–154 (ethyl acetate) | 73.7 |
| 9 | —N(piperidinyl) | 3 | Oxalate | 192–194 (methanol) | 67 |

EXAMPLES 10 TO 14

(1) The corresponding starting compounds are treated in the same manner as described in Example 1-(1), whereby the compounds shown in Table 3 are obtained.

TABLE 3

Structure: 5-$R^1$-substituted benzofuran with 7-CH₂—OH and 2-(Ring A) substituent

| $R^1$ | Ring A | m.p. (°C.) | Yield (%) |
|---|---|---|---|
| Cl | phenyl | 137–138.5 | 90 |
| CH₃O | phenyl | 149.5–151 | 94.2 |
| H | 4-Cl-phenyl | 139.5–140.5 | 95 |
| H | 4-CH₃-phenyl | 117–120 | 95 |
| H | 4-OCH₃-phenyl | 133–134.5 | 95 |

(2) The corresponding starting compounds are treated in the same manner as described in Example 1-(2), whereby the compounds shown in Table 4 are obtained.

TABLE 4

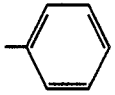

| R¹ | Ring A | m.p. (°C.) | Yield (%) |
|---|---|---|---|
| Cl | 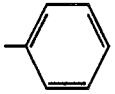 | 127–128.5 | 95 |
| CH₃O | 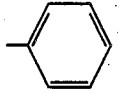 | 99–102 | 85.3 |
| H | 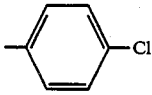 (−Cl) | 94–95.5 | 97.8 |
| H | 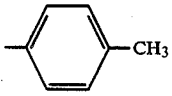 (−CH₃) | 93–96 | 73.2 |

TABLE 4-continued

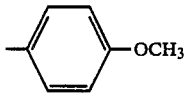

| R¹ | Ring A | m.p. (°C.) | Yield (%) |
|---|---|---|---|
| H | 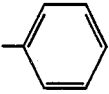 (−OCH₃) | 155–160 | 68.1 |

(3) The corresponding starting compounds are treated in the same manner as described in Example 2, whereby the compounds shown in Table 5 are obtained.

TABLE 5

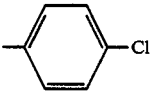

| Example Nos. | R¹ | Ring A | Salts | m.p. (°C.) | Yield (%) |
|---|---|---|---|---|---|
| 10 | Cl | 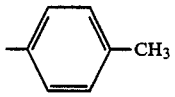 | HCl | 170–172 (ethanol) | 66.6 |
| 11 | CH₃O | 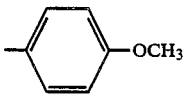 | oxalate | 153–156 (ethanol) | 84.7 |
| 12 | H | (−Cl) | HCl | 186.5–188 (ethanol) | 81.2 |
| 13 | H | (−CH₃) | HCl | 205–208 (ethanol-ether) | 60 |
| 14 | H | (−OCH₃) | HCl | 207–210 (ethanol-ether) | 65 |

EXAMPLE 15

7-Hydroxymethyl-2-phenylbenzofuran (1.57 g) is dissolved in dimethylsulfoxide (10 ml), and sodium hydride (60% oil dispersion) (0.57 g) is added thereto. After the mixture is stirred for 10 minutes, N-(2-chloroethyl)piperidine hydrochloride (1.35 g) is added to the mixture and the mixture is stirred at room temperature for 4 hours. The mixture is diluted with water and extracted with ethyl acetate. The extract is washed with water, dried and concentrated under reduced pressure to remove solvent. The residue is converted to its hydrochloride and recrystallized from ethyl acetate, whereby 7-[(2-piperidinoethoxy)methyl]-2-phenylbenzofuran hydrochloride (1.32 g) is obtained. Yield: 51%. m.p. 135°–136° C.

EXAMPLE 16

6-Hydroxymethyl-2-phenylbenzofuran (1.57 g), sodium hydride (60% oil dispersion) (0.57 g) and N-(3-chloropropyl)-piperidine hydrochloride (1.47 g) are treated in the same manner as described in Example 15, whereby 7-[(3-piperidinopropyloxy)methyl]-2-phenylbenzofuran oxalate (2.09 g) is obtained. Yield: 68%.

m.p. 178.5°–179.5° C. (recrystallized from methanol).

PREPARATION OF STARTING COMPOUND

Preparation 1

(1) A solution of 5-chloro-2-hydroxybenzoic acid (102 g) and hexamethylenetetramine (166 g) in trifluoroacetic acid is heated overnight. Dilute hydrochloric acid is added to the mixture and the mixture is heated. After cooling, the precipitates are collected by filtration, whereby 5-chloro-3-formyl-2-hydroxybenzoic acid (96.9 g) is obtained. m.p. 218° C.

(2) The product (193 g) obtained in paragraph (1) is dissolved in methanol, and the solution is saturated with hydrogen chloride. Thionyl chloride (100 ml) is added to the solution and the mixture is refluxed. After cooling, the precipitates are collected by filtration and dried, whereby methyl 5-chloro-3-formyl-2-hydroxybenzoate (190 g) is obtained. m.p. 132°–134° C.

(3) A mixture of the product (3.0 g) obtained in Paragraph (2), methyl α-bromophenylacetate (3.44 g), potassium carbonate (8.28 g) and dimethylformamide is heated. The mixture is acidified with hydrochloric acid and extracted with ethyl acetate. The extract is washed with water, dried and concentrated under reduced pressure to remove solvent. The residue is dissolved in ethanol, and potassium hydroxide (4.5 g) is added thereto. The mixture is refluxed and then concentrated under reduced pressure to remove solvent. Water is added to the residue, and the aqueous mixture is acidified with hydrochloric acid. The mixture is extracted with ethyl acetate and the extract is dried and concentrated under reduced pressure to remove solvent. Xylene and p-toluenesulfonic acid are added to the residue and the mixture is refluxed. The mixture is concentrated under reduced pressure to remove solvent, and the residue is dissolved in ethyl acetate. The solution is washed with water, dried and concentrated under reduced pressure to remove solvent. The residue is crystallized in isopropyl ether, whereby 5-chloro-2-phenylbenzofuran-7-carboxylic acid (2.32 g) is obtained. m.p. 255°–258° C.

2-hydroxy-5-methoxybenzoic acid (15 g) is treated in the same manner as described in Paragraph (1) to (3), whereby 5-methoxy-2-phenylbenzofuran-7-carboxylic acid (10.8 g) is obtained. m.p. 185°–187° C.

(4) 10% Palladium-carbon (500 mg) and ammonium formate (1.6 g) are added to a mixture of the product (1.46 g) obtained in Paragraph (3), ethyleneglycolmonomethyl ether and methanol, and the mixture is heated at 40° to 45° C. The mixture is filtered, and the filtrate is concentrated under reduced pressure to remove solvent. The residue is dissolved in ethyl acetate and the solution is washed, dried and concentrated under reduced pressure to remove solvent, whereby 2-phenylbenzofuran-7-carboxylic acid (1.0 g) is obtained. m.p. 212°–214° C.

Preparation 2

(1) A mixture of methyl 5-chloro-3-formyl-2-hydroxybenzoate (73.2 g), ethylene glycol (350 ml) and trimethylchlorosilane (129 ml) is stirred at room temperature for 2 hours. The reaction mixture is poured into a mixture of an aqueous saturated sodium bicarbonate solution and trimethylamine, and the mixture is extracted with ethyl acetate. The extracted is washed with water, dried and concentrated to remove solvent, whereby methyl 5-chloro-3-(1,3-dioxolan-2-yl)-2-hydroxybenzoate (86 g) is obtained as yellow powder.

(2) The product (86 g) obtained in Paragraph (1) is dissolved in a mixture of methanol (700 ml) and tetrahydrofuran (50 ml), and triethylamine (70 ml) and 10% palladium-charcoal (7 g) are added thereto. The mixture is subjected to catalytic hydrogenation under atmospheric pressure. The reaction mixture is filtered and the filtrate is concentrated to remove solvent. 10% Hydrochloric acid is added to the residue and the mixture is concentrated. Water is added to the residue and the aqueous mixture is extracted with ethyl acetate. The extract is dried and concentrated to remove solvent. The resultant crystals are collected, washed with cold ethanol and dried, whereby methyl 3-formyl-2-hydroxybenzoate (51.1 g) is obtained as colorless needles. m.p. 82°–84° C.

(3) A mixture of the product (2.0 g) obtained in Paragraph (2), methyl α-bromo-p-chlorophenylacetate (3.51 g), potassium carbonate (5.55 g) and dimethylformamide (60 ml) is heated at 70°–80° C. for 15 minutes and further heated at 100° C. for 10 minutes. The reaction mixture is filtered and washed with ethyl acetate. The washings and the filtrate are combined and water is added to the mixture. The mixture is acidified with 10% hydrochloric acid. The organic layer is collected and the aqueous layer is extracted with ethyl acetate. The organic layer and the extract are combined, washed with water, dried and concentrated to remove solvent. The residue is dissolved in ethanol (30 ml) and potassium hydroxide (3.25 g) is added thereto. The mixture is refluxed for one hour. The mixture is concentrated to remove solvent, and water is added to the residue. The aqueous mixture is acidified with 10% hydrochloric acid and extracted with ethyl acetate. The extract is washed with water, dried and concentrated to remove solvent. Xylene (100 ml) and p-toluenesulfonic acid (150 mg) are added to the residue and the mixture is refluxed for one hour. After cooling, ethyl acetate is added to the mixture, and the mixture is washed with water, dried and concentrated to remove solvent. The residue is recrystallized from ethyl acetate, whereby 2-(4-chlorophenyl)benzofuran-7-carboxylic acid (1.84 g) is obtained as colorless needles. m.p. 228°–230° C.

The corresponding starting compounds are treated in the same manner as described above, whereby the following compounds are obtained.

(i) 2-(4-methylphenyl)benzofuran-7-carboxylic acid m.p. 227°–229° C. (recrystallized from ethyl acetate-n-hexane)

(ii) 2-(4-methoxyphenyl)benzofuran-7-carboxylic acid m.p. 249°–250.5° C. (recrystallized from tetrahydrofuran-isopropyl ether)

What we claim is:

1. A benzofuran derivative of the formula:

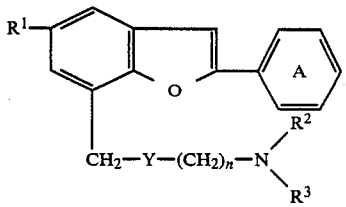

(I)

wherein R¹ is hydrogen atom, a lower alkoxy group or a halogen atom, one of R² and R³ is a lower alkyl group and the other is a lower alkyl group or a phenyl-lower alkyl group, or R² and R³ combine together with adjacent nitrogen atom to form a pyrrolidino group, piperidino group or morpholine group, Ring A is a phenyl group or a phenyl group substituted with a lower alkyl group, a lower alkoxy group or a halogen atom, Y is oxygen atom or sulfur atom and n is an integer of 2 or 3, or a pharmaceutically acceptable salt thereof.

2. The compound claimed in claim 1, in which R¹ is hydrogen atom, an alkoxy group of 1 to 4 carbon atoms or a halogen atom, one of R² and R³ is an alkyl group of 1 to 4 carbon atoms and the other is an alkyl group of 1 to 4 carbon atoms or a phenyl-alkyl group of 7 to 8 carbon atoms, or R² and R³ combine together with adjacent nitrogen atom to form pyrrolidino group, piperidino group or morpholino group, Ring A is phenyl group, methylphenyl group, methoxyphenyl group or chlorophenyl group.

3. The compound claimed in claim 1, in which R¹ is hydrogen atom, methoxy or chlorine, R² is methyl or ethyl, R³ is methyl, ethyl or benzyl, or R² and R³ combine together with adjacent nitrogen atom to form pyrrolidino, piperidino or morpholino group, Ring A is phenyl, 4-methylphenyl, 4-methoxyphenyl or 4-chlorophenyl.

4. The compound claimed in claim 3, in which R¹ is hydrogen or methoxy, R² and R³ combine together with adjacent nitrogen atom to form piperidino group, Ring A is phenyl, Y is sulfur atom and n is 2.

5. The compound claimed in claim 4 which is 2-phenyl-5-methoxy-7-(2-piperidinoethylthiomethyl)benzofuran or a pharmaceutically acceptable salt thereof.

6. The compound claimed in claim 4 which is 2-phenyl-7-(2-piperidinoethylthiomethyl)benzofuran or a pharmaceutically acceptable salt thereof.

7. A pharmaceutical composition which comprises a pharmaceutically effective amount of the compound claimed in claim 1 and a pharmaceutically acceptable carrier therefor.

8. A method for treatment or prophylaxis of pollakiuria, dyuria, nocturia, enuresis or irritable bladder in a warm-blooded animal, which comprises administering to the warm-blooded animal a therapeutically effective amount of the compound claimed in claim 1.

* * * * *